United States Patent [19]
Lin et al.

[11] Patent Number: 5,981,774
[45] Date of Patent: Nov. 9, 1999

[54] COMPOUNDS FOR THE TREATMENT OF HEPATOMA

[75] Inventors: Chun-Nan Lin, Kaohsiung; Shen-Jeu Won; Hsiao-Sheng Liu, both of Tainan; Shorong-Shii Liou, Nantou Hsien, all of Taiwan

[73] Assignee: National Science Council, Taipei, Taiwan

[21] Appl. No.: 08/948,264

[22] Filed: Oct. 9, 1997

Related U.S. Application Data

[60] Division of application No. 08/537,089, Sep. 29, 1995, Pat. No. 5,741,813, which is a continuation-in-part of application No. 08/134,834, Oct. 12, 1993, abandoned.

[30] Foreign Application Priority Data

Sep. 14, 1993 [JP] Japan .................................. 5-229248

[51] Int. Cl.$^6$ .................................................. C07D 311/86
[52] U.S. Cl. ........................................................ 549/392
[58] Field of Search ................................................ 549/392

[56] References Cited

U.S. PATENT DOCUMENTS 5,495,005  2/1996  Lin et al. ................................ 536/18.1

FOREIGN PATENT DOCUMENTS 07082263  3/1995  Japan .

*Primary Examiner*—Johann Richter
*Assistant Examiner*—Jane C. Osowecki
*Attorney, Agent, or Firm*—Bucknam and Archer

[57] ABSTRACT

Compounds of general Formula I in which the substituents of $R_1$–$R_7$ are hydrogen, hydroxy group, $C_{1-6}$ alkyl group, $C_{1-6}$ alkoxy group, or epoxypropoxy, but at the most, six of the substituents can simultaneously be hydrogen, methoxy group, or hydroxy group, or epoxypropoxy group for activity against hepatoma. There are also described processes for the preparation of the novel compounds and useful intermediates. Substitute benzophenones are described.

1 Claim, 18 Drawing Sheets

COMPOUNDS FOR THE TREATMENT OF HEPATOMA

This is Divisional of application Ser. No. 08/537,089, filed Sep. 29, 1995, now U.S. Pat. No. 5,741,813, which is a Continuation-in-part of U.S. Ser. No. 08/134,834 filed Oct. 12, 1993, abandoned.

FIELD OF THE INVENTION

The present invention relates to a series of novel γ-pyrone compounds which are active in the treatment of hepatoma, to processes for their preparation and to certain useful intermediates for the same processes.

BACKGROUND OF THE INVENTION

Based on the fact that the human body is susceptible to cancer, several methods to decrease or eliminate the painful illness, or to discover cytotoxic substances have been proposed.

Although many chemotherapeutic agents are clinically useful for the treatment of several forms of cancer such as acute leukemia, Burkitt's lymphoma, retinoblastoma, Ewing's sarcoma, testicular carcinoma, choriocarcinoma, Hodgkin's disease, lymphosarcoma, rhabdomyosarcoma, or mycosis fungoides, they are inactive against human hepatoma.

Some natural γ-pyrone compounds, Psorospermin (1) and related compounds, 3',4'-deoxy-psorospermin, 3',4'=deoxypsorospermin-3',4'-diol, 3',4'-deoxy-4'-chloropsorspermin-3'-ol, $O^5$-methyl-3',4'-deoxypsorospermin-3'-ol exhibit strong cytotoxic effects against leukemia cells (Habib, A. M. et al., 1987, J. Org. Chem. 52, 412–18). Recently Cushman, M. et al., reported the cytotoxicities of γ-pyrone compounds, flavonoid analogues (J. Nat. Prod., 54, 1656–60, 1991). The inventors have also discovered more potent and selective antitumor agents, which are γ-pyrone compound, cyclomorusin (2), cycloartomunin (3), dihydrocyclo-artomunin (4), artomunoxanth-otrione epoxide (7), dihydroisocycloartomunin (5), artomunoxanthone (6), cyclocommunol (8), cyclo-mulberrin (9), cyclocommunin (10) which were isolated and identified from the root bark of Formosan tripterospermum plants (Lin, C. N. et al., 1991, Phytochemistry, 30, 1669–1671; ibid, 1992, 31, 364–67, 2563–64, 2922–24), and have exhibited cytotoxic effects against human hepatoma PLC/PRF/5 and KB cells in vitro.

The name PLC/PRF/5 designates human primary liver cancer cells; the symbol KB designates epidermoid carcinoma cells.

SUMMARY OF THE INVENTION

The compounds of this invention have the general formula (I):

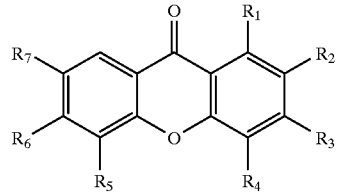

in which the substituents of $R_1$–$R_7$ are hydrogen, hydroxy group, $C_{1-6}$ alkyl group, $C_{1-6}$ alkoxy group, or epoxypropoxy, but at the most, six of the substituents can simultaneously be hydrogen, methoxy group, or hydroxy group, or epoxypropoxy group.

The invention also covers compounds of formula II:

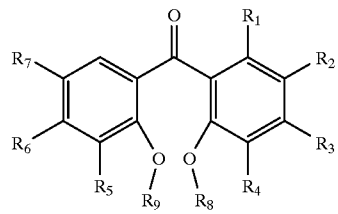

in which the substituents of $R_1$–$R_9$ are hydrogen, hydroxy group, $C_{1-6}$ alkyl group, $C_{1-6}$ alkoxy group, or epoxypropoxy group, but at the most, seven of the substituents are simultaneously hydrogen, methoxy group, hydroxy group, or epoxypropoxy group.

The compounds of formula (II) in which the substituents of $R_8$, $R_9$ are hydrogen, hydroxy group, or epoxypropoxy group, are preferred.

The synthesized compounds in this invention include xanthones of formula I and benzophenones of Formula II which are structurally related to the flavonoids.

The invention also covers methods of preparation of the above mentioned compounds.

A method of preparing compounds with the structure according to formula I, includes reacting a compound of formula III with a benzene, wherein the substituents of $R_5$–$R_7$, $R_9$ have the meaning defined above to obtain a compound of formula II and cyclizing the compound of formula II wherein the substituents of $R_1$–$R_9$, have the meaning defined above.

Further, a compound of formula I may be reacted with a phenol compound and hydrogen iodide wherein the substituents of $R_1$–$R_7$, can be hydroxy group to hydrolyze the alkoxy groups.

The reaction schemes are shown hereinbelow:

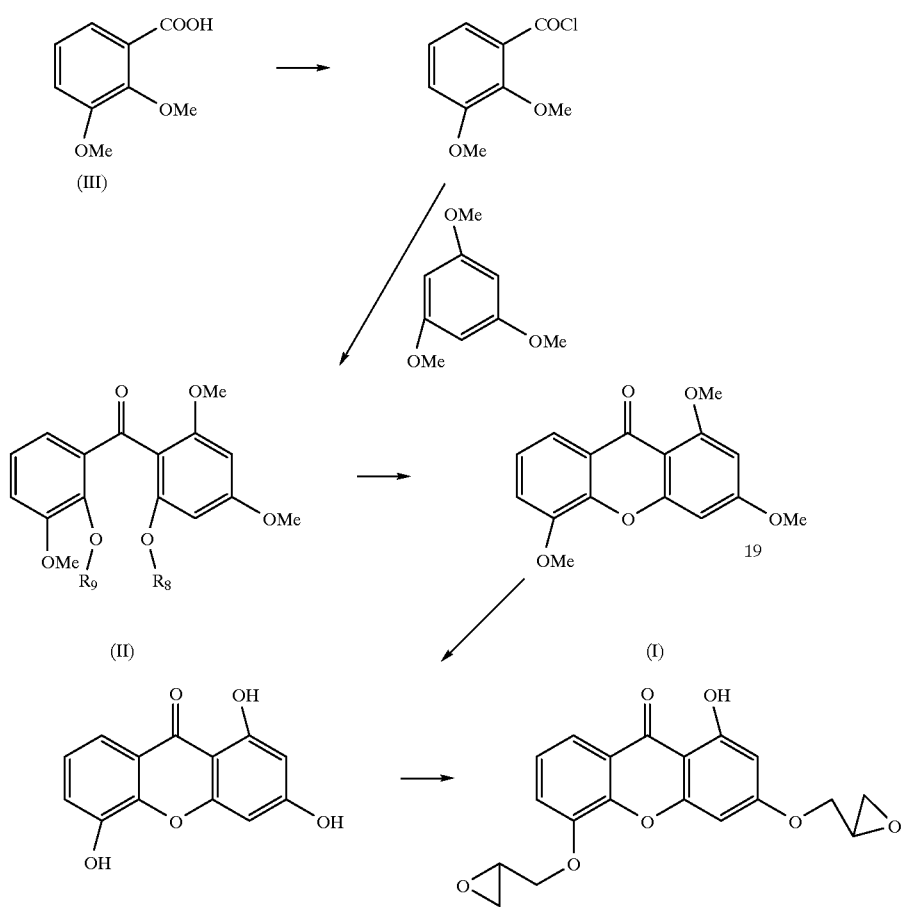
Tables I and 2 summarize some of the compounds of formula I and their properties.
TABLE 1
| example | compound | $R^1$ | $R^2$ | $R^3$ | $R^4$ | $R^5$ | $R^6$ | $R^7$ | ED$_{50}$ ($\mu$g/ml) KB | PLC/PRF/5 |
|---|---|---|---|---|---|---|---|---|---|---|
| 11 | 11 | OH | H | OH | H | H | OH | OH | NS | NS |
| 14 | 14 | H | H | OH | OH | H | OH | OH | NS | NS |
| 2 | 13 | H | H | OH | H | H | H | H | 0.77 | 3.75 |
| 3 | 14 | H | H | ![epoxide] | H | H | H | H | 0.85 | 1.43 |
| 4 | 15 | OH | H | H | H | H | ![epoxide] | H | NS | NS |

TABLE 1-continued

[Xanthone core structure with substituents R¹–R⁷]

|  |  |  |  |  |  |  |  |  | ED$_{50}$ ($\mu$g/ml) | |
|---|---|---|---|---|---|---|---|---|---|---|
| example | compound | R¹ | R² | R³ | R⁴ | R⁵ | R⁶ | R⁷ | KB | PLC/PRF/5 |
| 5 | 16 | H | [glycidyloxy] | H | H | H | [glycidyloxy] | H | 0.0043 | 0.23 |
|  | 17 | H | H | [glycidyloxy] | H | H | [glycidyloxy] | H | 0.11 | 0.24 |
| 8 | 21 | OH | H | [glycidyloxy] | H | [glycidyloxy] | H | H | 0.089 | 0.061 |
| Cisplatin |  |  |  |  |  |  |  |  | 0.16 | 5.29 | a For significant activity of the pure compound, an ED$_{50}$ < 4.0 ug/ml is required; n = 8
NS no dignificant activity

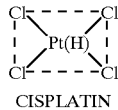
CISPLATIN

TABLE 2

[Xanthone core structure with substituents R¹–R⁷]

| example | compound | R¹ | R² | R³ | R⁴ | R⁵ | R⁶ | R⁷ | chemical formula | mp (°C.) |
|---|---|---|---|---|---|---|---|---|---|---|
| 11 | 11 | OH | H | OH | H | H | OH | OH | C$_{17}$H$_{16}$O$_6$ | >300 |
| 14 |  | H | H | OH | OH | H | OH | OH | C$_{17}$H$_{16}$O$_6$ | >300 |
| 2 | 13 | H | H | OH | H | H | H | H | C$_{13}$H$_8$O$_3$ | 241~242 |
| 3 | 14 | H | H | [glycidyloxy] | H | H | H | H | C$_{16}$H$_{12}$O$_4$ | 157~158 |
| 4 | 15 | OH | H | H | H | H | [glycidyloxy] | H | C$_6$H$_{12}$O$_5$ | 153~154 |
| 5 | 16 | H | [glycidyloxy] | H | H | H | [glycidyloxy] | H | C$_{19}$H$_{16}$O$_6$ | 170~171 |
|  | 17 | H | H | [glycidyloxy] | H | H | [glycidyloxy] | H | C$_{19}$H$_{16}$O$_6$ | 187~188 |

TABLE 2-continued

| example | compound | R¹ | R² | R³ | R⁴ | R⁵ | R⁶ | R⁷ | chemical formula | mp (°C.) |
|---------|----------|-----|-----|-----------------|-----|-----------------|-----|-----|------------------|----------|
| 8 | 21 | OH | H | 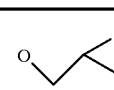 | H | 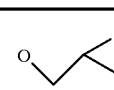 | H | H | $C_{19}H_{16}O_7$ | 180~182 |

As shown in the above reaction schemes, a benzoyl chloride is reacted with a benzene by Friedel-crafts acylation to yield a benzophenone precursor, and then cyclization is carried out to yield a xanthone. Various epoxyproxy derivatives of xanthones of formula I can be produced by reaction in an alkaline aqueous solution with epichlorohydrin in excess amount. Methoxybenzoylchloride was obtained from monomethoxylbenzoic acid as the starting material, then reacted with dimethoxybenzene yielding a trimethoxyxanthone. Based on this method 2,3-dimethoxylbenzoic acid as the starting material, yielded a benzophenone of formula II as the intermediate which then yielded the xanthone compound (I). In the intermediates benzophenone of formula II the substituents of R8 and R9 may be hydrogen, methoxy, R1–R7 may be hydrogen, hydroxy, $C_{1-6}$ alkyl, $C_{1-6}$ alkoxy group, or epoxypropoxy group. This synthetic method also includes preparation of the benzophenone compounds, the latter may be reacted with tetramethylammonium hydroxide, to yield xanthone compounds in which the substituents may be hydroxy, methoxy, or epoxyproxy which obtained from reaction of the hydroxyxanthone with epichlorohydrin.

The purified compounds were identified by UV, IR, $^1$H-NMR, $^{13}$C-NMR, EIMS and physical properties.

PLC/PRF/5 cells were isolated from human hepatoma and are known to produce HBs Ag continuously in culture fluids. The cells were grown as continuous cultures in a growth medium consisting of Dulbecco's modified Eagle medium (DMEM, GIBCO, Grand Island, N.Y.), 10% fetal bovin serum (FBS, GIBCO), 100 IU/ml penicillin, 100 g/ml streptomycin and 2 mM L-glutamine. The KB cells were maintained on DMEM containing 10% FBS L-glutamine and antibiotics. For the microassay, the growth medium was supplemented further with 10 mM Hepes buffer, pH 7.3.

The microassay for anticellular effect was performed as described in Ito (1984) J. Interferon Res. 4,604,608. The $ED_{50}$ values were calculated from a semilog plot of the drug concentration vs. the percentage of viable cells on day 4.

The results are listed in Table 1 and Table 2 and show chemical data and cytotoxicity (ED50 values in $\mu g/ml^{-1}$) of γ-pyrones; d=equals no significant activity. For significant activity of the pure compound, an ED50 less than 4.0 $\mu g/ml^{-1}$ is required; N=8. A=2,3-epoxy propoxy.

Although compound 13 showed significant and potent inhibitory activity against human hepatoma PLC/PRF/5 and KB cells in vitro, the $ED_{50}$ values are 3.73 $\mu g/ml$ and 0.77 $\mu g/ml$. Compound 14 was epoxidized from 13, it enhanced very markedly the inhibitory effects against human hepatoma PLC/PRF/5 cells in vitro. The epoxidation took place at 2,6-OH, 3,6-OH of formula I, and showed significant inhibitory effect against human hepatoma PLC/PRF/5 and KB cells in vitro. The compound 2,6-di(2,3-epoxypropoxy) xanthone component (16) showed more potent inhibitory activity against KB cells in vitro, the $ED_{50}$ values were over 40 times that of cisplatin. On the other hand, the compounds 21 epoxidized from 1,3,5-tri-hydroxy-xanthone, showed significant novel inhibitory activity against human hepatoma PLC/PRF/5 and KB cells in vitro. Based on the above results, it is clearly indicated that the compounds of this invention having an additional epoxide group substituents in the xanthone or benzophenone structure show novel inhibitory activity.

The novel two types of compounds γ-pyrone, together with a conventional adjuvant, carrier, or diluent, may be placed into the form of pharmaceutical compositions and unit dosages thereof. In such forms, they may be employed as solids or liquids for oral use; in the form of suppositories for rectal administration; in the form of sterile injectable solutions for parenteral (including subcutaneous) use. The solid pharmaceutical dosages may comprise disintegrating agents such as starch, sodium carboxymethyl-cellulose, and/or binders such as ethyl alcohol, glycerin, and/or carriers such as magnesium stearate, lactose, which are prepared by conventional pharmaceutical methods. The sterile injectable solution preparations can be adjusted with buffers, such as phosphates, if desired, with auxiliary agents, and emulsifiers.

The novel pharmaceutical compositions in unit dose form are very useful in the treatment of hepatoma. The novel compounds of the invention may accordingly be administered to a living subject, including a human, and should be adjusted according to the complexity of the symptoms. The preferred individual dosage is 50 to 300 mgs for oral administration and 2 to 15 mgs for intravenous administration and can be administered up to 3 times daily.

A typical tablet which may be prepared by conventional tabletting techniques contains:

| | |
|---|---|
| active compound | 40 mg |
| lactose | 30 mg |
| starch | 8 mg |
| magnesium stearate | 10 mg |
| corn starch | 12 mg |
| | 100 mg |

EXAMPLE 1

Preparation of 2-Hydroxy-4,6-dimethoxy-2',3'-dimethoxybenzophenone (18 a) and 2,4,6-trimethoxy-2'-hydroxy-3'-methoxybenzophenone (18 b)

2,3-dimethoxybenzoic acid (1.8 g, 9.89 mmol) in dry $C_6H_6$ (25 ml) was treated with 3.5 ml of oxalyl chloride under an argon atmosphere and through stirring at room temperature.

After 5 hrs the solvent and the excess reagent were removed under reduced pressure. The residue, 2,3-dimethoxybenzoyl chloride was dissolved in anhydrous $Et_2O$ (40 ml) and 1,3,5-trimethoxybenzene (1.6 g, 9.52 mmol) and $AlCl_3$ (4.0 g) were added. After stirring 15 hrs at room temperature, the mixture was hydrolyzed with ice-$H_2O$ (300 ml) containing concentrated HCl (35 mL), and extracted with $CH_2Cl_2$. Solvent removal gave a crude product that was purified by column chromatography(silica gel-$CH_2Cl_2$) to yield pale yellow oil (MeOH) (18), 2.9 g (9.5 mmol, 92%)

The product is a mixture of the two compounds 18a and 18b.

$^1$H-NMR (CDCl$_3$): δ3.70 (12H, s, 4 OMe), 3.86 (6H, s, 2 OMe), 3.91 (6H, s, 2 OMe), 6.16 (4H, s, H-3 and H-5 of 18a and 18b), 6.72 (2H, t, J=8.0, H-4' of 18a and 18b), 6.91–7.06 (4H, m, H-5$^1$ and H-6' of 18a and 18b), 12.51 (2H, s, 2 OH of 18a and 18b, D$_2$O exchangeable).

EXAMPLE 2

Preparation of 3-hydroxyxanthone (13)

1.6 g (7.08 mmol) of methoxyxanthone was refluxed at 160° C. in a mixture of hydrogen Iodide (35 ml) and phenol (42 ml) for 8 hours. The resulting mixture was then poured into NaHSO$_3$ aqueous solution and generated a yellow precipitate.

The precipitate was collected and purified with a silica gel column by chromatography (Eluted with chloroform-methanol, 4:1). 1.40 g (6.60 mmol) of 3-hydroxyxanthone, a yellow needles, were crystallized from methanol. The yield was 93%. The data of the physical properties are listed below.

mp: 241–242° C.

MS (m/z, %): 212 (100) (M$^+$);

UV λmax (MeOH) nm (log ε): 235 (4.06), 265 (3.39), 330 (3.59); λmax (MeOH+NaOAc) nm (log ε): 230,265 (sh), 335;

IR (KBr): 3115, 1615 cm$^{-1}$ $^1$H-NMR (DMSO): see Table 3

Anal. ($C_{13}H_8O_3$) C,H.

EXAMPLE 3

Preparation of 3-(2,3-Epoxypropoxy)xanthone (14)

To a solution of 0.19 g (4.71 mmol) of sodium hydroxide in 6.18 ml of isopropanol and 1.3 ml of water, 1.00 g (4.72 mmol) of 3-hydroxyxanthone (5H) and 3.76 ml (46.86 mmol) of epichlorohydrin were added. The components were reacted under stirring at 70° C. for 2 hours. The resulting mixture was filtered to remove a dimer side product a glycidyl ether. The filtrate was concentrated at reduced pressure at 50~60° C. and 10 ml of isopropanol was added to the mixture to yield more of the dimer which was filtered off from hot mixture. The clear filtrate was allowed to cool, and the thus formed solid was then washed with 1.40 ml of isopropanol and dried in air to give 945 mg (4.46 mmol) of brown product. The yield was 74%. Purified by chromatography on silica gel and crystallized from dichloromethane, a colorless powder of 3-(2,3-epoxypropoxy)xanthone was obtained. The data of physical properties are listed below.

mp: 157–158° C.;

MS (m/z) %: 268 (100) (M$^+$);

IR (KBr): 1645, 1265 cm$^1$;

$^1$H-NMR (CDCl$_3$): δ2.79–2.99 (m, CH$_2$ of epoxy ring), 3.42 (m, 1H, CH of epoxy ring), 4.05 (dd, J=11, 6.0 Hz, 1H), 4.39 (dd, J=11, 3.0 Hz, 1H), 6.91 (d, J=2.4 Hz, 1H, H-4), 6.95 (dd, J=9.0, 2.4Hz, 1H, H-2), 7.27–7.47 (m, 2H, H-6 and H-7), 7.65–7.70 (m, 1H, H-5), 8.26 (d, J=9.0 Hz, 1H, H-1), 8.32 (dd, J=9.0, 1.5 Hz, 1H, H-8);

$^{13}$C-NMR (CDCl$_3$) 644.5 (CH$_2$ of epoxy ring), 69.2 (OCH$_2$), 49.7 (CH of epoxy ring), 101.1 (C-4), 113.4(C-2), 116.2 (C-8b), 117.7 (C-5), 121.9(C-8a), 123.9 (C-7), 126.6 (C-8), 128.4(C-1), 134.3 (C-6), 156.2 (C-4b), 157.9(C-4a), 163.7 (C-3), 176.2 (CO);

Anal: ($C_{16}H_{12}O_4$) C,H.

EXAMPLE 4

Preparation of 6-(2,3-Epoxypropoxy)-1-Hydroxyxanthone (15)

To a solution of 0.42 g (10.5 mmol) of sodium hydroxide in 3 ml of water was added 50 ml of 2-propanol and the 1.2 g (5.26 mmol) of 1,6-dihydroxyxanthone. To the above mixture was then added 10 ml (124.63 mmol) of epichlorohydrin, and the mixture was heated at 70° C. for 3 hrs with stirring.

The hot reaction mixture was filtered to remove the dimeric byproduct the glycidyl ether. The filtrate was concentrated under reduced pressure at 50 to 60° C. The semisolid residue was treated with 20 ml of refluxing 2-propanol and more of the dimer was filtered off from the hot mixture. The clear filtrate, on cooling, yielded a solid. This was collected, washed with 3 ml of 2-propanol, air-dried and yielded a tan-colored product. It was purified by column chromatography (silica gel-CH$_2$Cl$_2$) and crystallized from CH$_2$Cl$_2$ to give yellow powder (15), 1.4 g (4.93 mmol, 94%).

MS(m/z) %: 284 (100) (M$^+$);

IR (KBr): 3450, 1650, 1630 cm$^{-1}$ $^1$-NMR (CDCl$_3$): δ2.81 (1H, dd, J=11, 6.0 Hz, CH$_2$ in the epoxide ring), 2.91 (1H, t, J=5 Hz, CH$_2$ in the epoxide ring), 3.42 (1H, m, CH in the epoxide ring), 4.04 (1H, dd, J=11, 6.0 Hz, OCH$\underline{H}$), 4.43 (1H, dd, J=11, 3.0 Hz, OCH$\underline{H}$), 6.78 (dd, J=9.0 Hz, 1.0 Hz,1H, H-2), 6.88 (2H, m, H-4, H-5), 6.97 (1H, dd, J=9.0, 2.5 Hz, H-7), 7.55 (1H, t, J=9.0 Hz, H-3), 8.16 (1H, d, J=9.0 Hz, H-8), 12.75 (1H, s, 1-OH, exchange with D$_2$O); (Wu, E. S. C. et al 1989);

$^{13}$C-NMR (CDCl$_3$): δ44.5 (CH$_2$ in the epoxide ring), 49.7 (CH in the epoxide ring), 69.4 (OCH$_2$), 100.9 (C-5), 106.8 (C-4), 108.4 (C-8b), 110.2 (C-2), 113.7 (C-7), 114.7 (C-8a), 127.6 (C-8), 136.2 (C-3), 156.3 (C-4a), 158.0 (C-4b), 161.9 (C-1), 164.4 (C-6), 181.3 (CO);

Anal. ($C_{16}H_{12}O_5$) C.H

EXAMPLE 5

Preparation of 2,6-di(2,3-epoxypropoxy) xanthone (16)

To a solution of 0.42 g (10.5 mmol) of sodium hydroxide in 3 ml Of 2,6-dihydroxyxanthone. To the above mixture was then added 10 ml (124.63 mmol) of epichlorhydrin, and the mixture was treated as in example 3 to yield a colorless powder (16), 1.2 g (3.85 mmol, 73%).

MS (m/z)%: 340 (100) (M$^+$);

IR (KBr): 1655, 1620 cm$^{-1}$;

$^1$H-NMR (CDCl$_3$): δ2.81 (2H, m, CH$_2$ in the epoxide ring), 2.96 (2H, dd, J=10,4.5 Hz, CH$_2$ in the epoxide ring), 3.42 (2H, M, 2×CH in the epoxide ring), 4.01 (1H, dd, J=11, 6.0 Hz, OCHH), 4.05 (1H, dd, J=11, 6.0 Hz, OCHH), 4.38 (1H, t, J=3 Hz, OCHH), 4.43 (1H, t, J=3 Hz, OCHH), 6.91 (1H, d, J=2.5 Hz, H-5), 6.97 (1H, dd, J=9.0, 2.5 Hz, H-3), 7.35 (1H, dd, J=9.0, 2.5 Hz, H-7), 7.41 (1H, d, J=9.0 Hz, H-4), 7.68 (1H, d, J=2.5 Hz, H-1), 8.26 (1H, dd, J=9.0 Hz, H-8), (Wu, E. S. C. et al 1989);

$^{13}$C-NMR (CDCl$_3$): δ44.5, 44.6 (CH$_2$ in the epoxide ring), 49.8, 50.0 (CH in the epoxide ring), 69.3, 69.4 (OCH$_2$), 100.9 (C-5), 106.9 (C-1), 113.5 (C-7), 115.6 (C-8a), 119.3 (C-4), 122.2 (C-8b), 124.6 (C-3), 128.3 (C-8), 151.2 (C-4a), 154.8 (C-2), 157.8 (C-4b), 163.7 (C-5), 176.0 (CO).

Anal. (C$_{19}$H$_{16}$O$_6$) C,H

EXAMPLE 6

Preparation of 1,3,5-trimethoxyxanthone (19)

The mixture of the compounds 18a and 18b (2.9 g, 9.15 mmol) from Example 1 was treated with pyridine (52.8 ml), H$_2$O (26.4 mL) and aqueous 10% tetramethylammonium hydroxide (18 mL). The mixture was refluxed 34 hrs, poured into ice, acidified with HCl, and extracted with Et$_2$O, yielding an oil which, after purification by column chromatography (silica gel-CH$_2$Cl$_2$) and crystallized from CH$_2$Cl$_2$ yielded colorless powder (19), 2.03 g (7.10 mmol, 78%).

mp: 233–235° C.;

$^1$H-NMR (CDCl$_3$): δ3.89, 3.96, 4.00 (3s, 9H, 3 Ome), 6.34 (1H, d, J=2.5 Hz, H-2), 6.62 (1H, d, J=2.5 Hz, H-4), 7.13–7.28 (2H, m, H-6 and H-7), 7.86 (1H, dd, J=9.0,1.5 Hz, H-8),

EXAMPLE 7

Preparation of 1,3,5-trihydroxyxanthone (20)

A mixture of compound 19 (1.9 g, 6.64 mmol) phenol (42 ml) and HI (35 ml) was refluxed at 160° C. for 8 hour and the reaction mixture was poured into aqueous NaHSO$_3$ solution. The resulting yellow precipitate, was collected, purified by silica gel column chromatography (CH$_2$Cl$_2$—MeOH, 4:1), and crystallized from methanol to give pale yellow needles 20, 1.41 g (5.78 mmol, 87%).

mp: 211–213° C.;

$^1$H-NMR, CDCl$_3$): δ6.19 (1H, d, J=2.0 Hz, H-2), 6.39 (1H, d, J=2.0 Hz, H-4), 7.07–7.19 (2H, m, H-6 and H-7), 7.62 (1H, dd, J=9.0,2.5 Hz. H-8).

EXAMPLE 8

Preparation of 3,5-di(2,3-epoxypropoxy)-1-hydroxyxanthone (21)

To a solution of 0.28 g (5.0 mmol) of potassium hydroxide in 3 ml of water was added 25 ml of 2-propanol and the 1.3 g (5.33 mmol) of 1,3,5-trihydroxyxanthone. To the above mixture was the added 7.5 ml (93.47 mmol) of epichlorohydrin, and the mixture was treated as example 4 to yield a pale yellow powder (MeOH) (21), 0.45 g (1.26 mmol, 35%)

MS (m/z) %: 356 (100) (M$^+$);

IR (KBr): 3500,1670, 1620 (cm$^{-1}$);

$^1$H-NMR (CDCl$_3$): δ1.61–2.78 (2H, m, CH$_2$ in the epoxide ring), 2.94–3.01 (2H, m, CH$_2$ in the epoxide ring), 3.41 (1H, m, CH in the epoxide ring), 3.50 (1H, m, CH in the epoxide ring), 4.03 (1H, dd, J=11,6.0 Hz, OCHH), 4.11 (1H, dd, J=11,6.0 Hz, OCHH), 4.35 (1H, dd, J=11 3.0 Hz, OCHH), 4.48 (1H, dd, J=11 3.0 Hz, OCHH), 6.38 (1H, d, J=2.5 Hz, H-2), 6.57 (1H, d, J=2.5 Hz, H-4), 7.30 (2H, m, H-6 and H-7), 7.85 (1H, dd, J=9.0, 2.5 Hz, H-8) (Wu, E. S. C. et al 1989);

$^{13}$C-NMR (CDCl$_3$): δ44.6 (2 CH$_2$ in the epoxide ring), 49.7 and 50.1 (2 CH in the epoxide ring), 69.2 and 70.6 (2 OCH$_2$), 93.5 (C-4), 97.9 (C-2), 104.2 (C-8b), 117.7 (C-8), 118.0 (C-6), 122.0 (C-8a), 123.6 (C-7), 147.2 (C-4b and C-5), 157.5 (C-4a), 163.4 (C-1), 165.4 (C-3), 180.8 (CO);

Anal: Anal. (C$_{19}$H$_{16}$O$_7$) C,H

EXAMPLE 9

Preparation of 3,6-di(2,3-epoxypropxy)xanthone (17)

To a solution of 0.42 g (10.5 mmol) sodium hydroxide in 3 mL water was added 50 mL 2-propanol and then 1.2 g (5.26 mmol) of 3,6-dihydroxyanthone. To the above mixture was then added 10 mL (124.63 mmol) of epichlorohydrin, and the mixture was treated as for 15 to yield a colourless powder (CH$_2$Cl$_2$) (17), 1.4 g (4.49 mmol, 85%); MS, m/z (%) 340 (100) (M$^+$); IR (KBr) 1650, 1620 cm$^{-1}$; $^1$H NMR (CDCl$_3$): σ2.81 (2 H, dd, J=4.8, 2.5 Hz, CH$_2$ in the epoxide ring), 2.97 (2 H, t, J=4.8 Hz, CH$_2$ in the epoxide ring), 3.42 (2 H, m, 2×CH in the epoxide ring), 4.05 (2H, dd, J=11, 6.0 Hz, 2×OCHH), 4.39 (2H, dd, J=11, 3.0 Hz, 2×OCHH), 6.89 (2H, d), J=2.5 Hz, H-4 and H-5), 6.97 (2H, dd, J=9.0, 2.5 Hz, H-2 and H-7), 8.24 (2H, d, J=9.0 Hz, H-1 and H-8 (Wu et al 1989); $^{13}$C NMR (CDCl$_3$): σ44.6 (2CH$_2$ in the epoxide ring), 49.8 (2CH in the epoxide ring), 69.3 (2 OCH$_2$), 101.2 (C-4 and C-5), 113.1 (C-2 and C-7), 116.2 (C-8a and C-8b), 128.3 (C-1 and C-8), 157.9 (C-4a and C-4b), 163.4 (C-3 and C-6), 175.4 (CO) (Chaudhuri et al 1978; Frahm & Chaudhuri 1979; Biemann 1989); Anal (C$_{19}$H$_{16}$O$_6$) C, H.

2-Hydroxy-4-methoxy-2'-methoxybenzophenone, 4a 2,4-dimethoxy-2'-hydroxybenzophenone, 4b To a solution of 2.0 g (13.14 mmol) of 2-methoxybenzoic acid in 60 ml of dry benzene, 5 ml oxalyl chloride was added under stirring at room temperature. After 2 hours, solvent and excess reagents were removed at reduced pressure. The residual 2-methoxybenzoyl chloride was dissolved in 80 ml of anhydrous ether, and then 1.8 g (13.03 mmol) of 1,3-dimethoxybenzene and 5.0 g of aluminum chloride were added. After stirred at room temperature for 8 hours, the resulting mixture was hydrolyzed by 500 ml of ice water containing 45 ml of concentrated HCl and then extracted with chloroform. The solvent was removed to give a crude product. After purified by column chromatography, 2.20 g (8.53 mmol) of a yellow oily product was obtained and the yield was 65%. The data of the physical properties of the compounds were measured and are listed below. The product was a mixture of the compounds 4a and 4b.

$^1$H NMR (CDCl$_3$): δ3.76, 3.82 (2s, 12H), 6.33 (dd, J=8.5, 2.4Hz, 2H), 6.47 (d, J=2.4Hz, 2H), 7.01 (m, 4H, aromatic H), 7.24 (m, 4H, aromatic H), 7.42 (m, 2H, aromatic H), 12.72 (s, 2H).

According to the method of production of 2-hydroxy-4-methoxy-2'-methoxybenzophenone (4a) and 2,4-dimethoxy- 2'-hydroxybenzophenone (4b), 2.00 g (13.14 mmol) of 2-methoxybenzoic acid was reacted with 2.19 g (13.04 m mol) of 1,3,5-trimethoxy benzene to give 2.20 g (7.75 mmol) of 3,4-dimethoxy-2-hydroxy-2'-methoxybenzophenone and 2,3,4-trimethoxy-2'-hydroxybenzophenone. Then, described in example 3, 1.35 g (5.92 m mol) of 3,4-dihydroxybenzophenone as pale yellow powder was produced. The physical properties were measured and are listed below.

mp: 238–240° C.

MS(m/z) %: 228 (100) (M+);

UV λmax (MeOH) nm (log ε): 207(3.80) 237(4.18), 255(4.08), 285 (sh) (3.49), 315 (3.74); λmax (MeOH+NaOAc+$H_3BO_3$) nm (log ε) 208, 235, 265, 285(sh), 320;

IR (KBr): 3200, 1640 cm$^{-1}$;

$^1$H-NMR (CDCl$_3$): δ6.94 (1H, d, J=8.5 Hz, H-2), 7.41–7.46 (1H, m, H-7), 7.57 (1H, d, J=8.5 Hz, H-1), 7.63 (1H, m, H-6), 7.80–7.86 (1H, m, H-5), 8.15 (1H, dd, J=8.5, 1.5 Hz, H-8)

Anal. ($C_{13}H_8O_4$) C,H.

Based on the examples described above, the following compounds are produced.

tripteroside $R_1=R_3=R_7=OH$, $R_6=O$—GLU.
norathyrol $R_1=R_3=R_6=R_7=OH$,

| | |
|---|---|
| 1,3-Dihydroxyxanthone | $R_1 = R_3 = OH$ |
| 1,3,6,7-tetrahydroxy xanthone | $R_1 = R_3 = R_6 = R_7 = OH$ |
| 2,3-Dimethoxyxanthone | $R_1 = R_3 = OCH_3$ |
| 2,3-Dihydroxyxanthone | $R_2 = R_3 = OH$ |
| 3,4,6,7-tetrahydroxy xanthone) | $R_3 = R_4 = R_6 = R_7 = OH$ |
| 3,4-Dimethoxyxanthone | $R_3 = R_4 = OCH_3$ |
| 1,6-Dimethoxyxanthone | $R_1 = R_6 = OCH_3$ |
| 3,5-Dimethoxyxanthone | $R_3 = R_5 = OCH_3$ |
| 3,5-Dihydroxyxanthone | $R_3 = R_5 = OH$ |
| 2,6-Dimethoxyxanthone | $R_2 = R_6 = OCH_3$ |
| 1,6-Dimethoxyxanthone | $R_1 = R_6 = OCH_3$ |
| 1,6-Dihydroxyxanthone | $R_2 = R_6 = OH$ |
| 3,6-Dimethoxyxanthone | $R_3 = R_6 = OCH_3$ |
| 2,6-Dimethoxyxanthone | $R_2 = R_6 = OCH_3$ |
| 2,6-Dihydroxyxanthone | $R_2 = R_6 = OH$ |
| 3,6-di(2,3-epoxypropoxy) xanthone | $R_3 = R_6 = $ epoxypropoxy |
| 3,6-Dimethoxyxanthone | $R_3 = R_6 = OCH_3$ |
| 3,6-Dihydroxyxanthone | $R_3 = R_6 = OH$ |

| Formula (2) | |
|---|---|
| 28 | 4,6-Dimethoxy-2-hydroxy-2'-methoxybenzophenone |
| 29 | 2,4,6-trimethoxy-2'-hydroxybenzophenone |
| 30 | 4,5-Dimethoxy-2-hydroxy-2'-methoxybenzophenone |
| 31 | 2,4,5-trimethoxy-2'-hydroxybenzophenone |
| 32 | 3,4-Dimethoxy-2-hydroxy-2'-methoxybenzophenone |
| 33 | 2,3,4-trimethoxy-2'-hydroxybenzophenone |
| 34 | 2-Hydroxy-4-methoxy-2',3'-dimethoxybenzophenone |
| 35 | 2,4-dimethoxy-2'-hydroxy-3'-methoxybenzophenone |
| 36 | 2-Hydroxy-6-methoxy-2',4'-dimethoxybenzophenone |
| 37 | 2,6-dimethoxy-2'-hydroxy-4'-methoxybenzophenone |
| 38 | 2-Hydroxy-5-methoxy-2',4'-dimethoxybenzophenone |
| 39 | 2,5-dimethoxy-2'-hydroxy-4'-methoxybenzophenone |
| 40 | 2-Hydroxy-4-methoxy-2',4'-dimethoxybenzophenone |
| 41 | 2,4-dimethoxy-2'-hydroxy-4'-methoxybenzophenone |
| 42 | 3,4-Dimethoxy-2-hydroxy-2',4',5'-trimethoxybenzophenone |
| 43 | 2,3,4-trimethoxy-2'-hydroxy-4',5'-dimethoxybenzophenone |

The activity of compounds 16, 17 and 21 on macromolecular synthesis were determined by measuring the isotopic incorporation of [$^3$H]-thymidine, -uridine and -methionine in the human PLC/PRF/5 and KB cells respectively.

PLC/PRF/5 cells were obtained from human hepatoma and are known to produce HBs Ag continuously in culture fluids. Human hepatoma PLC/PRF/5 and epidermis carcinoma KB cells were maintained in Dulbeceo's modified Eagle medium (DMEM, Gibco BRL Grand Island, N.Y., U.S.A.), containing 10% fetal bovine serum (FBS, Gibco BRL), 2 mM L-glutamine, 100 units mL-1 penicillin, 100 μg mL-l streptomycin. The 212 cells were maintained in Minimum essential alpha medium (MEM, Gibco BRL), containing 10% calf serum (Gibco BRL). For microassay, the growth medium was supplemented with 10 mM HEPES buffer, pH 7.3 and incubated at 37° C. in a $CO_2$ incubation.

Inhibition of Macromolecular Synthesis. The synthesis of macromolecules were measured by the incorporation of $^3$H-thymidine, -uridine or -methionine (New England) Nuclear, Boston, Mass., USA) into the tumor cells. Briefly, the tumor cell (1 1.5×10$^4$/100 μl/well) maintained in growth medium with or without drugs in microplates were incubated at 37° C. The cells after pulsed labeling with [$^3$H]-thymidine, -uridine, or -methionine for 18 hrs at day 4 post-treatment were harvested and loaded onto glass filter paper (Skatron. Va., USA). The incorporation activities of the cells were measured by the liquid scintillation counter (LS-5000 TA, Beckman Calif., USA). All treatments were conducted in quadruplicate and the mean values were used for analysis. Each experiment was repeated at least 3 times. The data shown are mean counts per minute (CPM)±SEM. Percent inhibition of [$^3$H]-thymidine, -uridine, or -methionine incorporation was calculated as follows:

$$\% \text{ inhibition} = \left(1 - \frac{\text{Test CPM}}{\text{Control CPM}}\right) \times 100$$

Figure 1A:
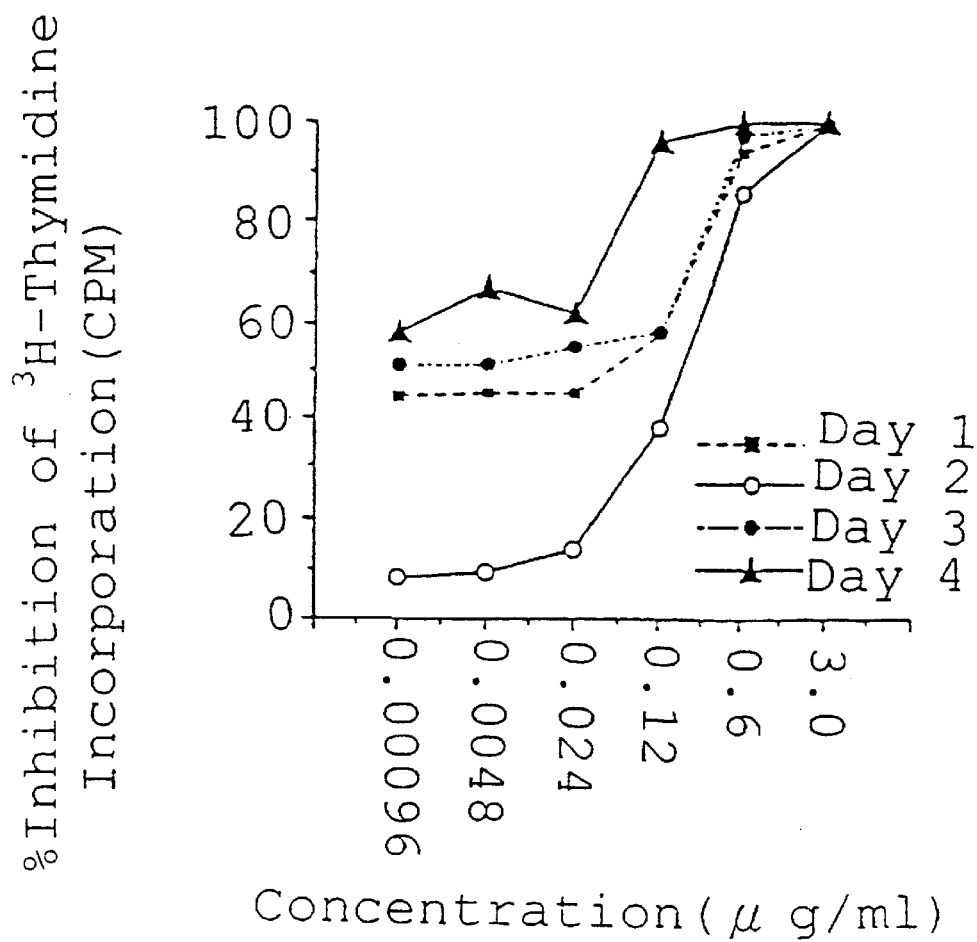
FIG. 1A illustrates the % inhibition of $^3$H-Thymidine incorporation with variation in concentration and time of compound 16 in human PLC/PRF/5 cell.
Figure 1B:
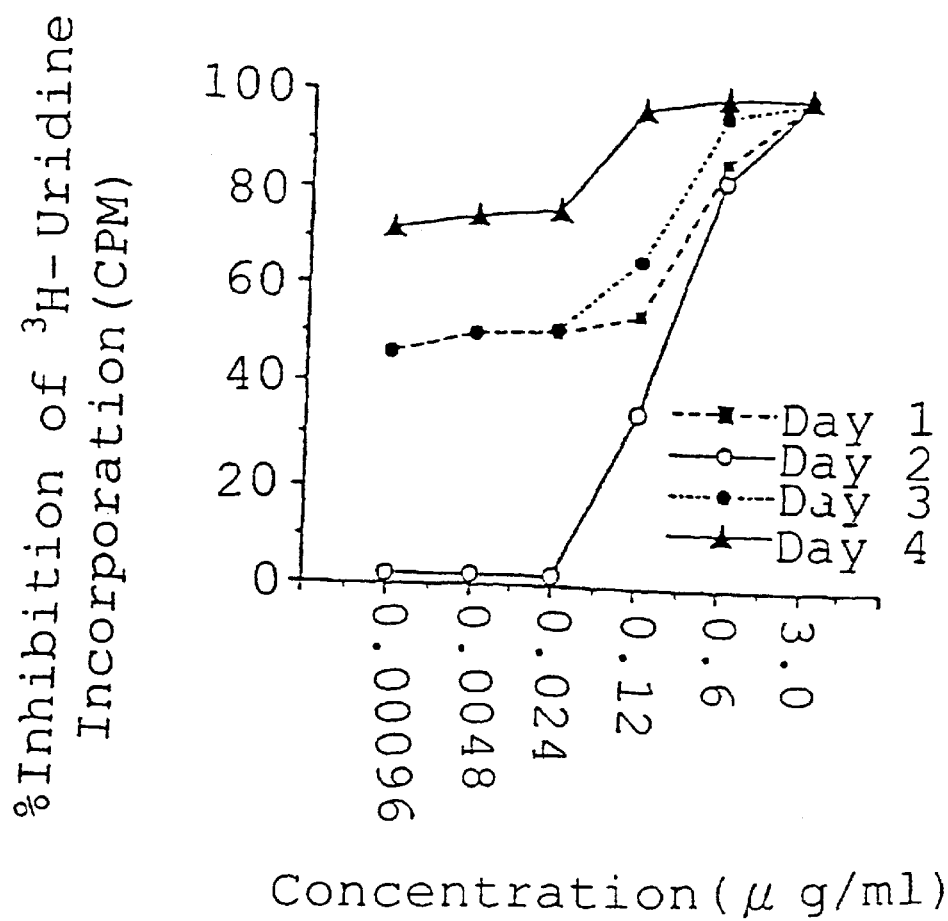
FIG. 1B illustrates the % inhibition of $^3$H-uridine incorporation with variation in concentration and time of compound 16 in human PLC/PRF/5 cell.
Figure 1C:
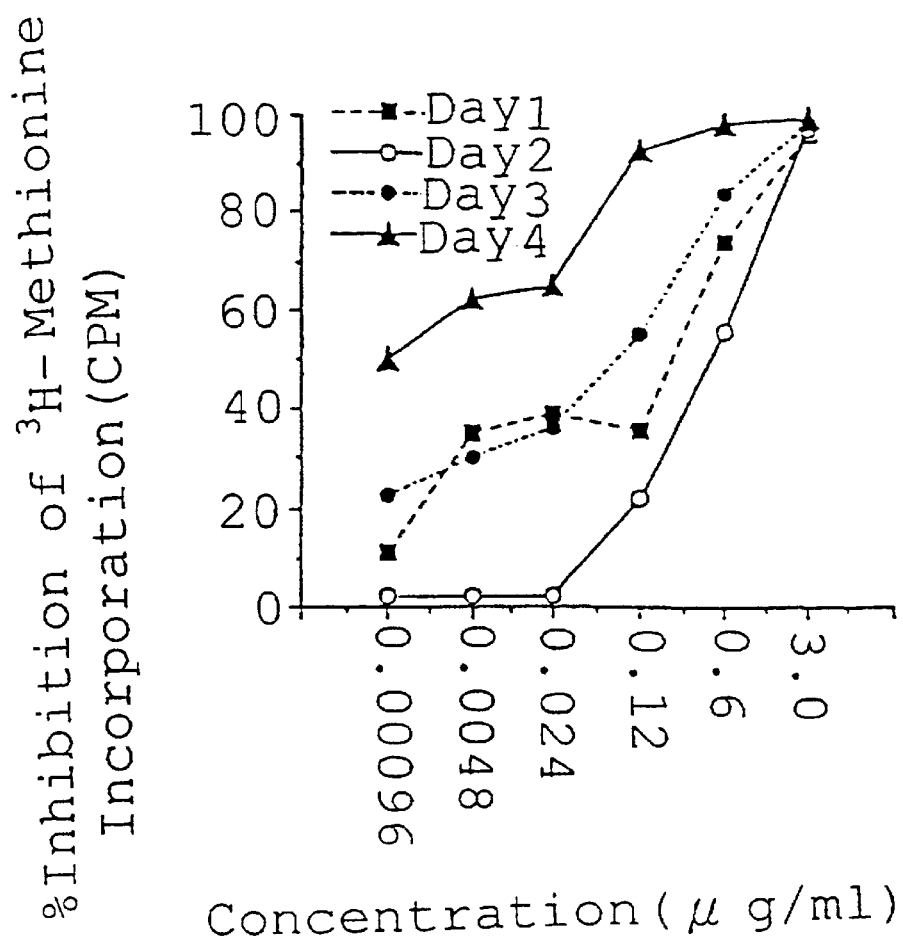
FIG. 1C illustrates the % inhibition of $^3$H-Methionine incorporation with variation in concentration and time of compound 16 in human PLC/PRF/5 cell.
Figure 2A:
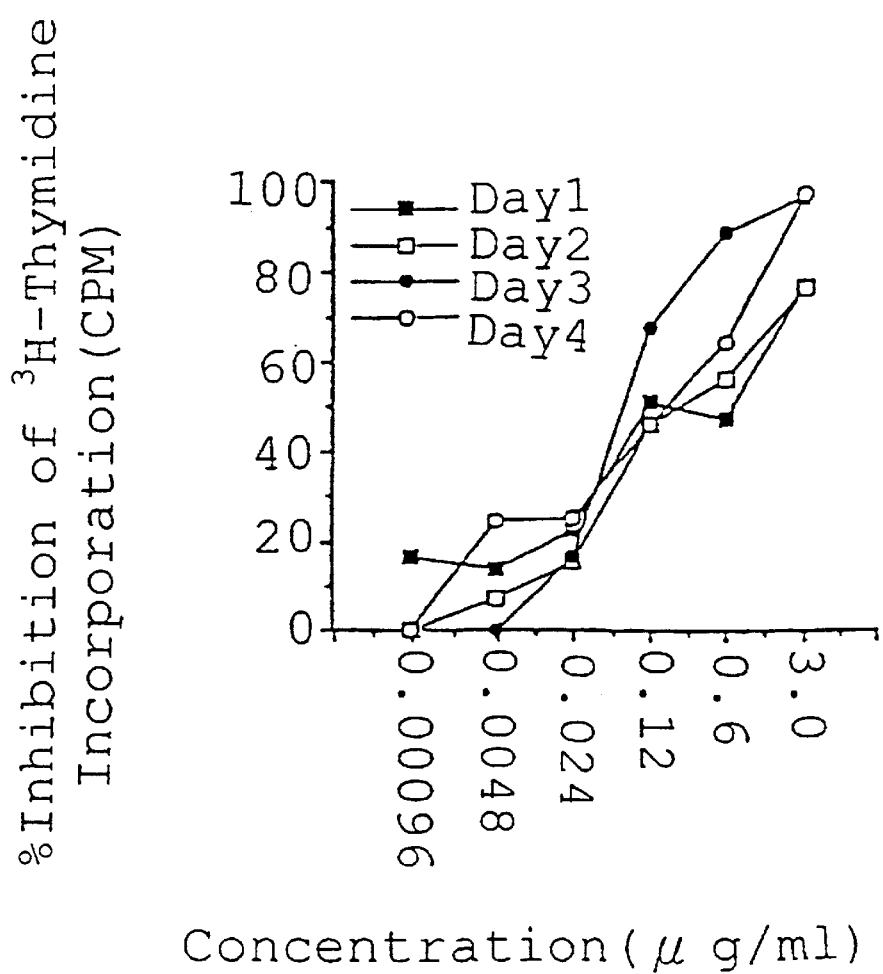
FIG. 2A illustrates the % inhibition of H-Thymidine incorporation with variation in concentration and time of compound 16 in epidermis carcinoma KB cell.
Figure 2B:
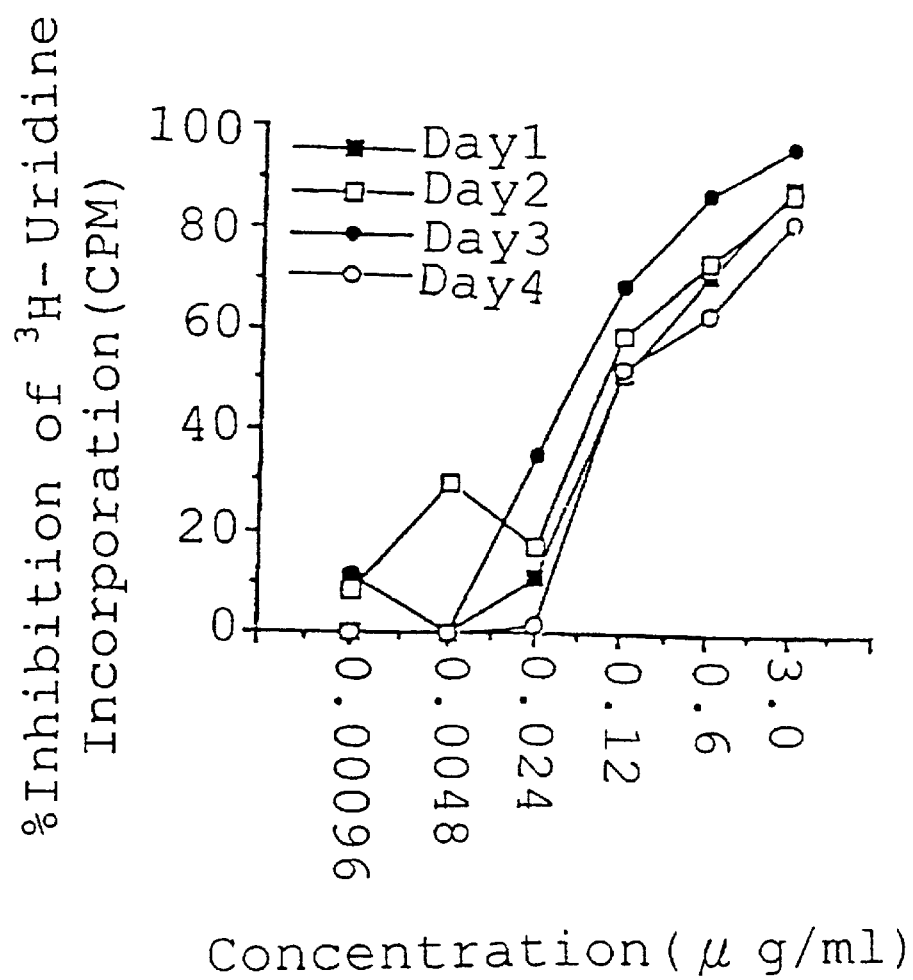
FIG. 2B illustrates the % inhibition of $^3$H-Uridine incorporation with variation in concentration and time of compound 16 in epidermis carcinoma KB cell.
Figure 2C:
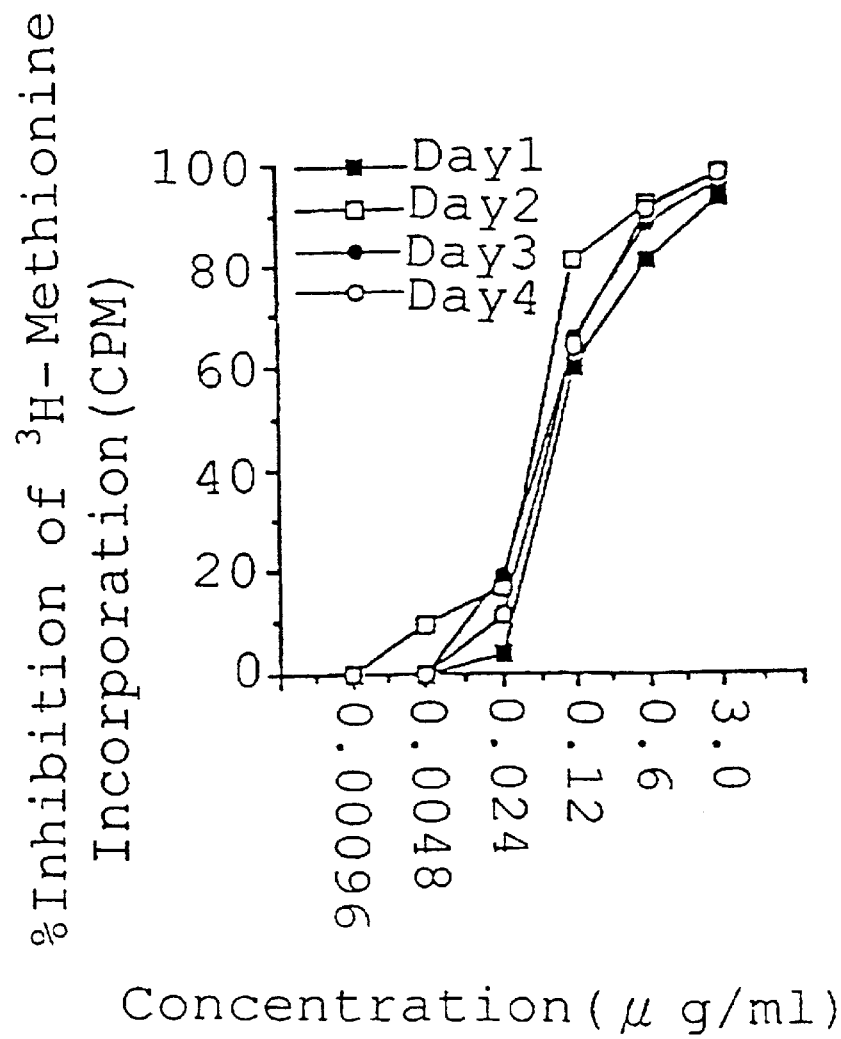
FIG. 2C illustrates the % inhibition of $^3$H-Methionine incorporation with variation in concentration and time of compound 16 in epidermis carcinoma KB cell.
Figure 3A:
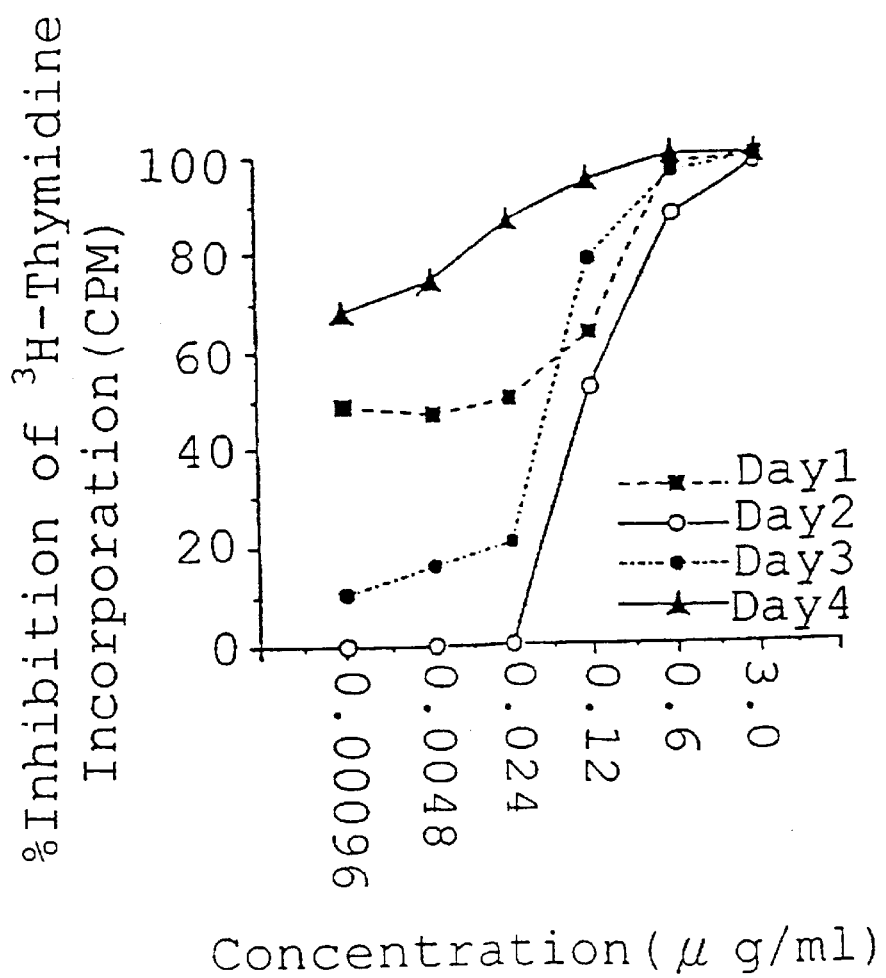
FIG. 3A illustrates the % inhibition of $^3$H-Thymidine incorporation with variation in concentration and time of compound 17 in human PLC/PRF/5 cell.
Figure 3B:
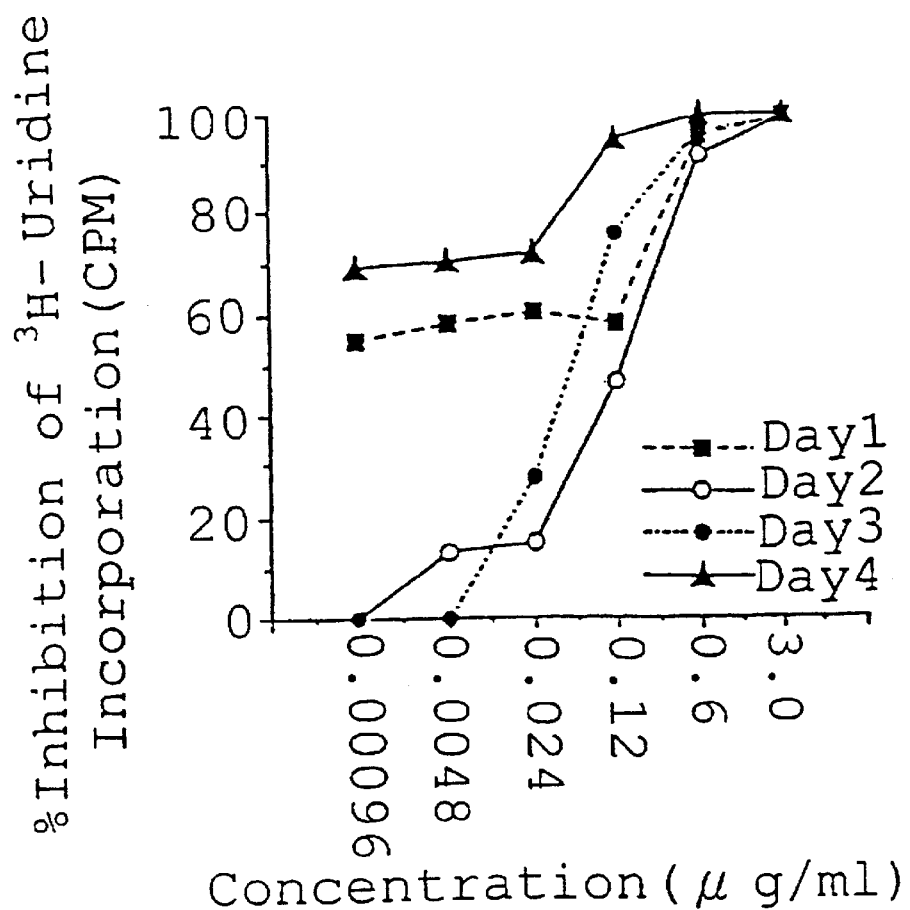
FIG. 3B illustrates the % inhibition of $^3$H-Uridine incorporation with variation in concentration and time of compound 17 in human PLC/PRF/5 cell.
Figure 3C:
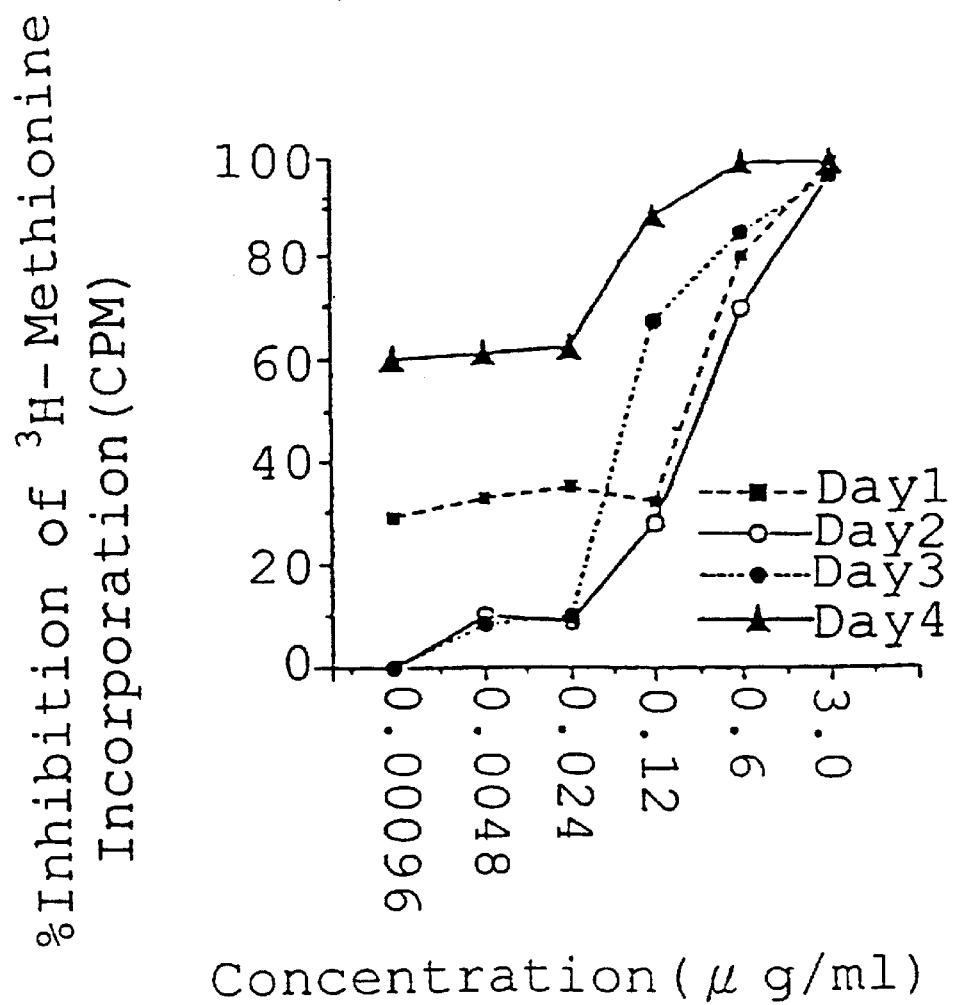
FIG. 3C illustrates the % inhibition of $^3$H-Methionine incorporation with variation in concentration and time of compound 17 in human PLC/PRF/5 cell.
Figure 4A:
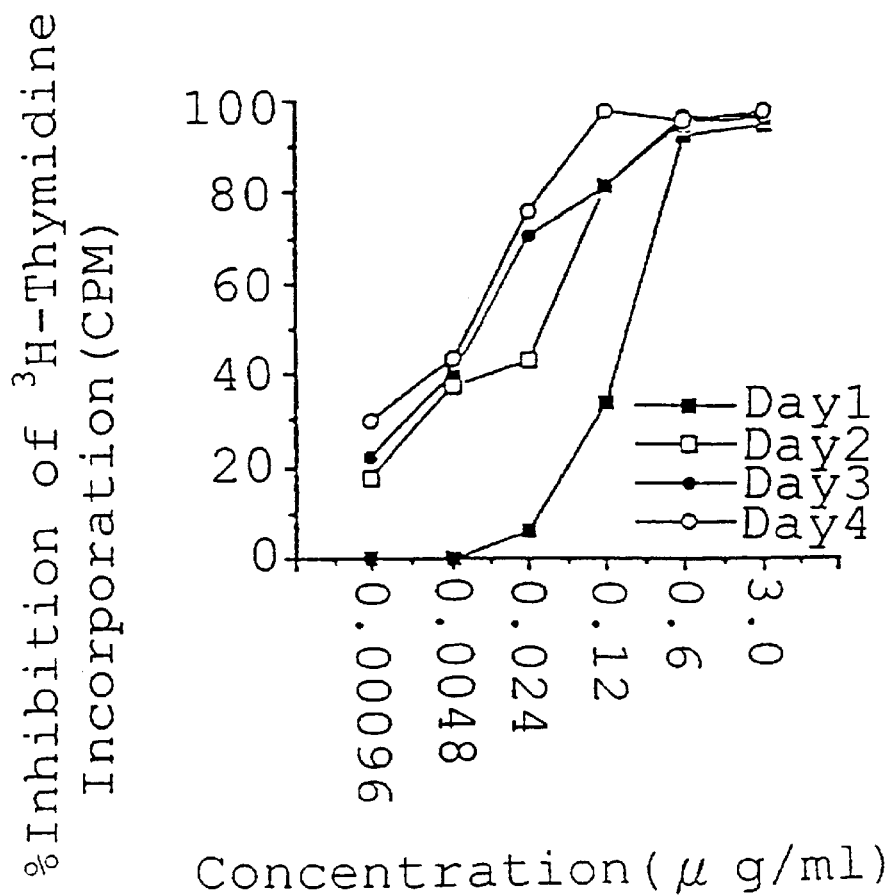
FIG. 4A illustrates the % inhibition of $^3$H-Thymidine incorporation with variation in concentration and time of compound 17 in epidermis carcinoma KB cell.
Figure 4B:
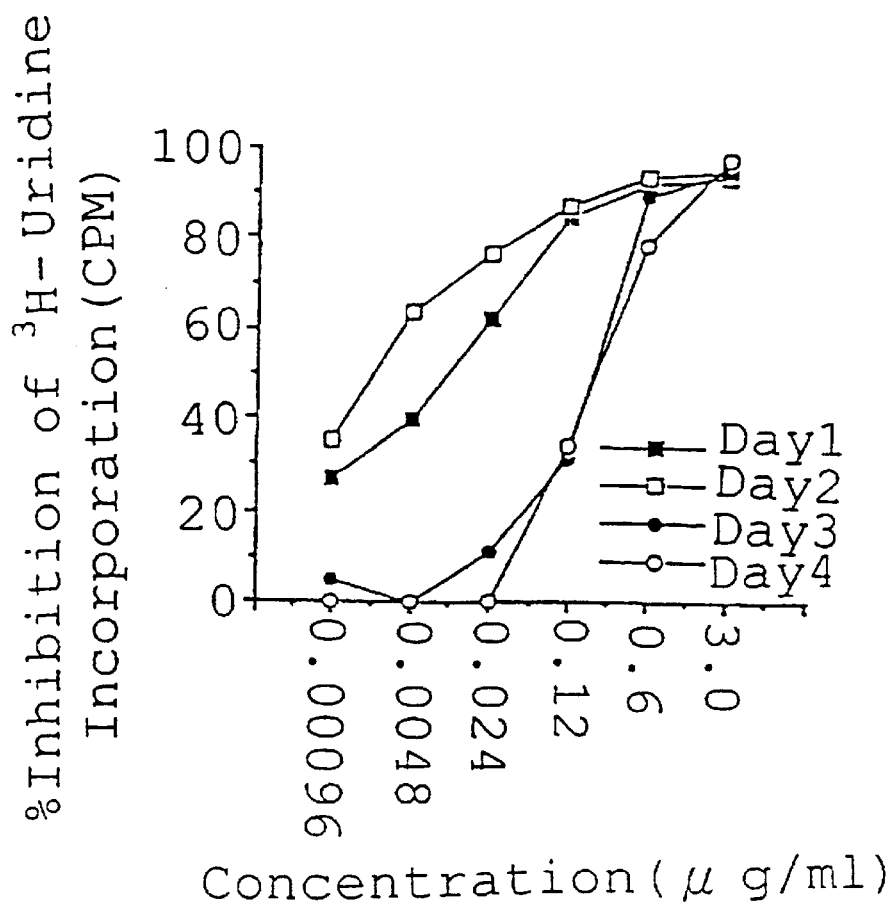
FIG. 4B illustrates the % inhibition of $^3$H-Uridine incorporation with variation in concentration and time of compound 17 in epidermis carcinoma KB cell.
Figure 4C:
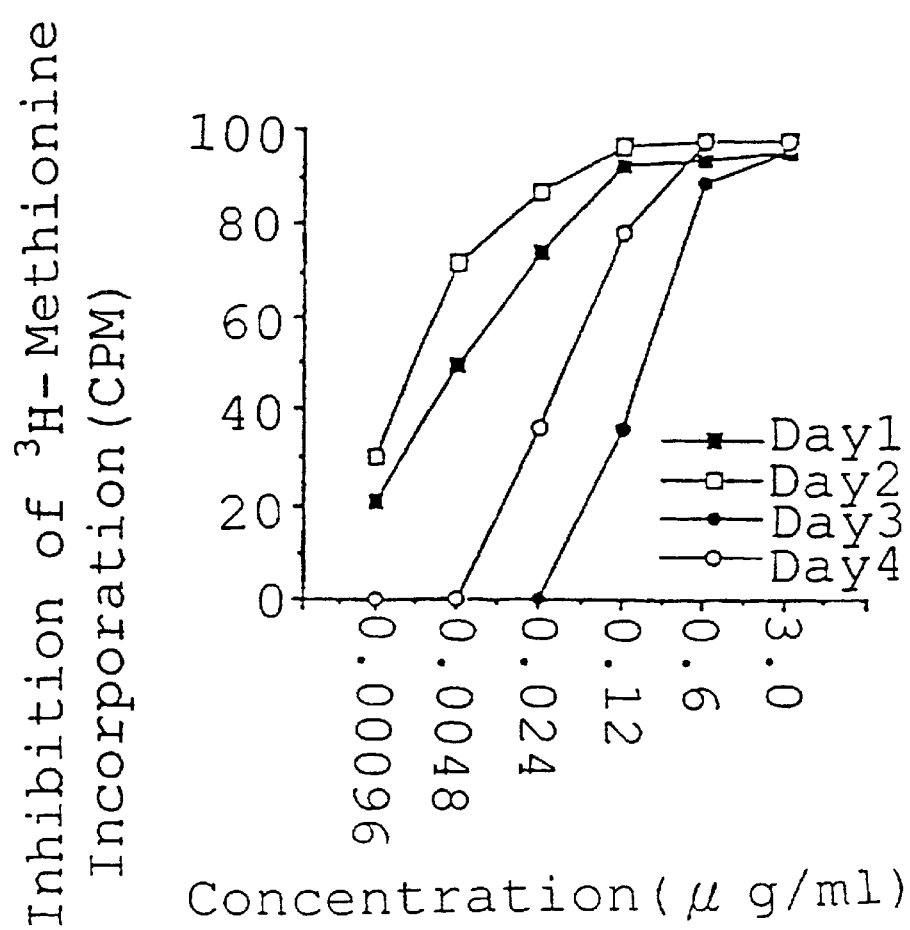
FIG. 4C illustrates the % inhibition of $^3$H-Methionine incorporation with variation in concentration and time of compound 17 in epidermis carcinoma KB cell.
Figure 5A:
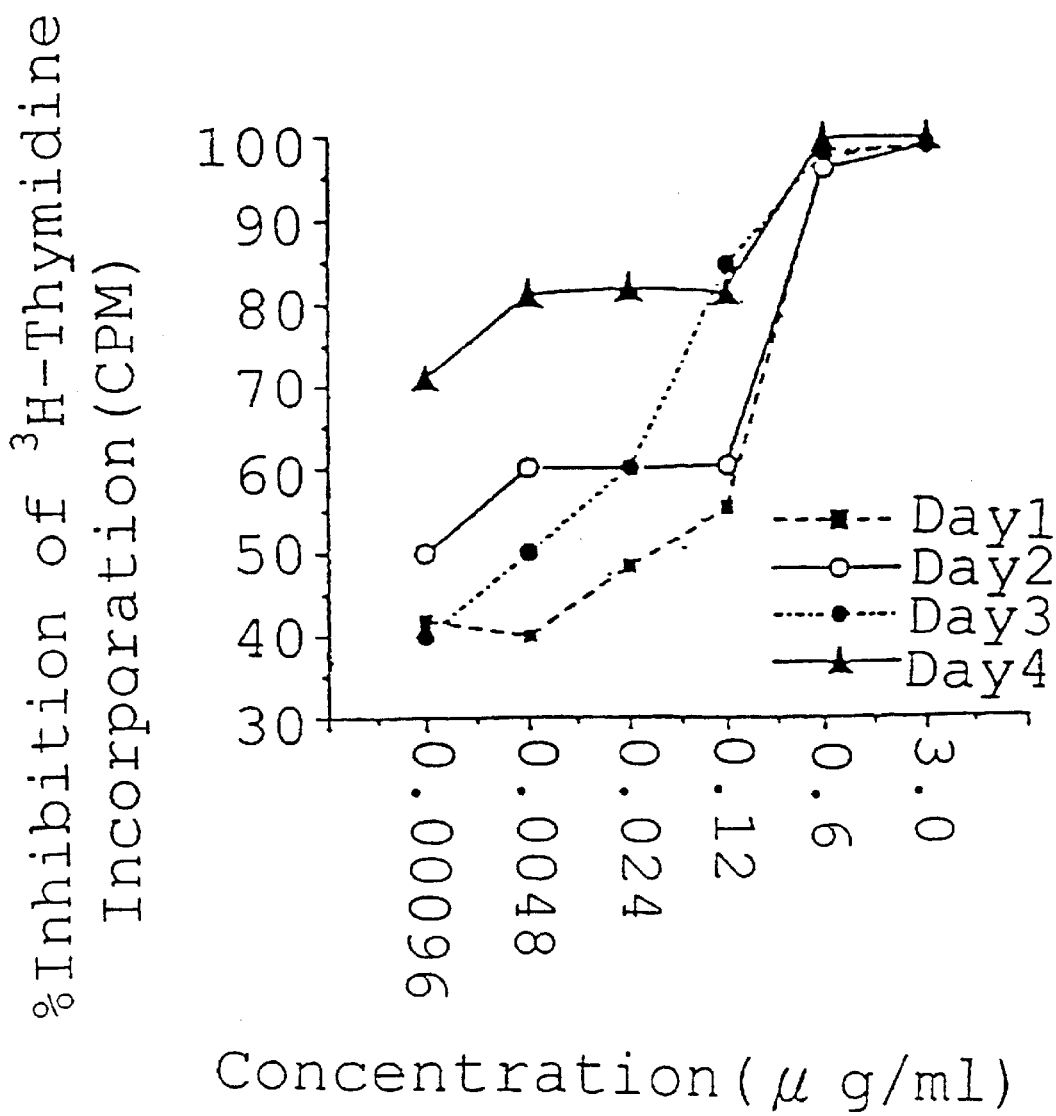
FIG. 5A illustrates the % inhibition of $^3$H-Thymidine incorporation with variation in concentration and time of compound 21 in human PLC/PRF/5 cell.
Figure 5B:
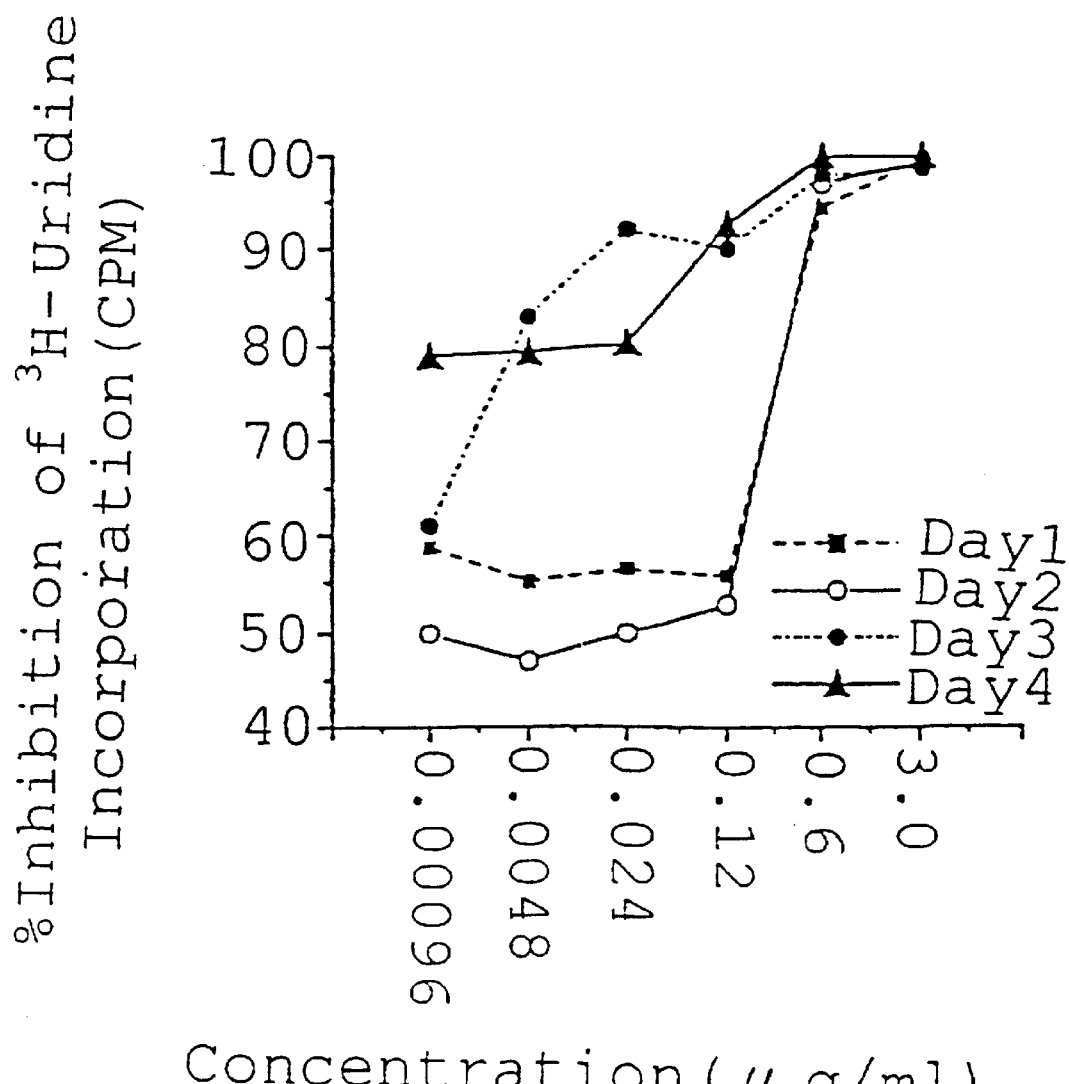
FIG. 5B illustrates the % inhibition of $^3$H-Uridine incorporation with variation in concentration and time of compound 21 in human PLC/PRF/5 cell.
Figure 5C:
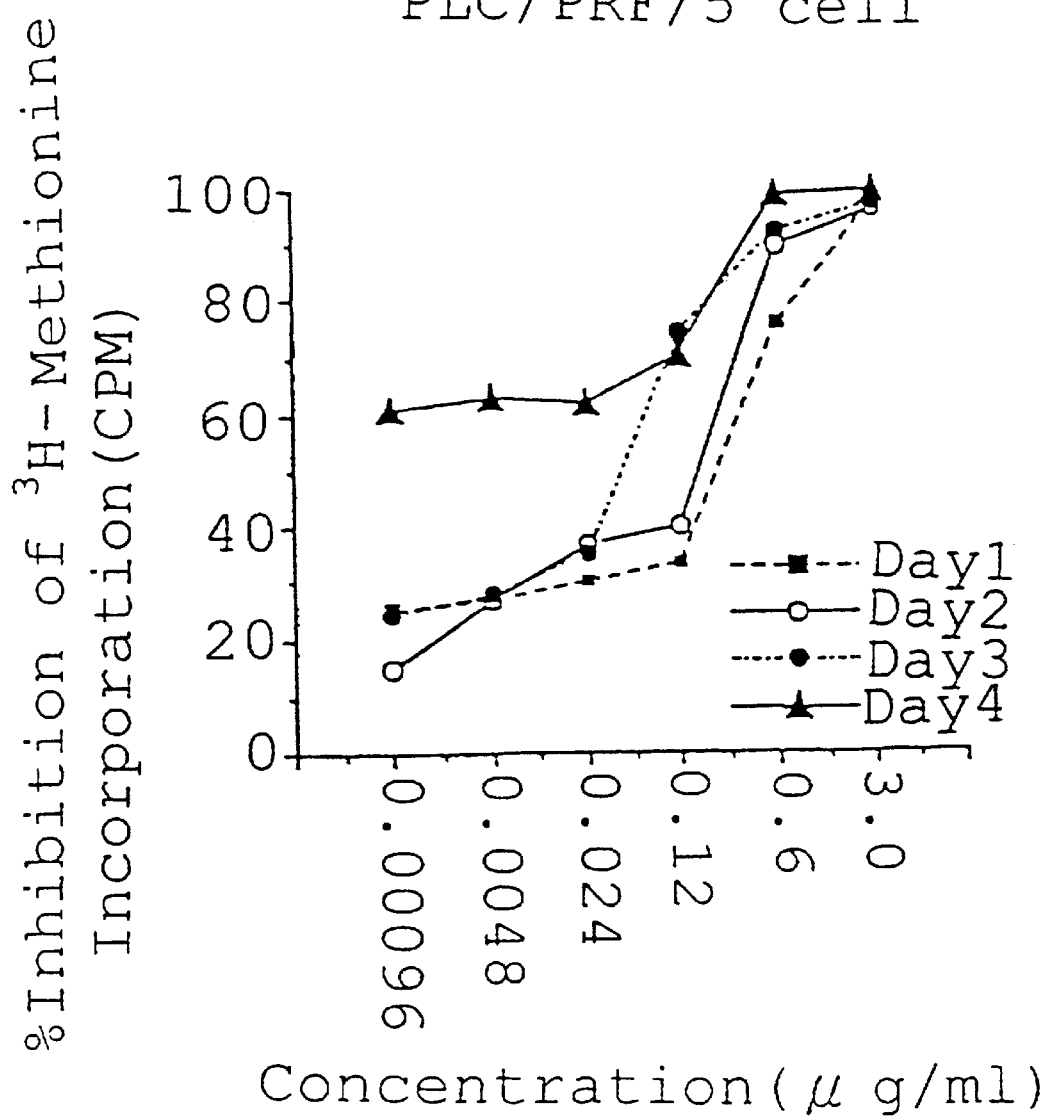
FIG. 5C illustrates the % inhibition of $^3$H-Methionine incorporation with variation in concentration and time of compound 21 in human PLC/PRF/5 cell.
Figure 6A:
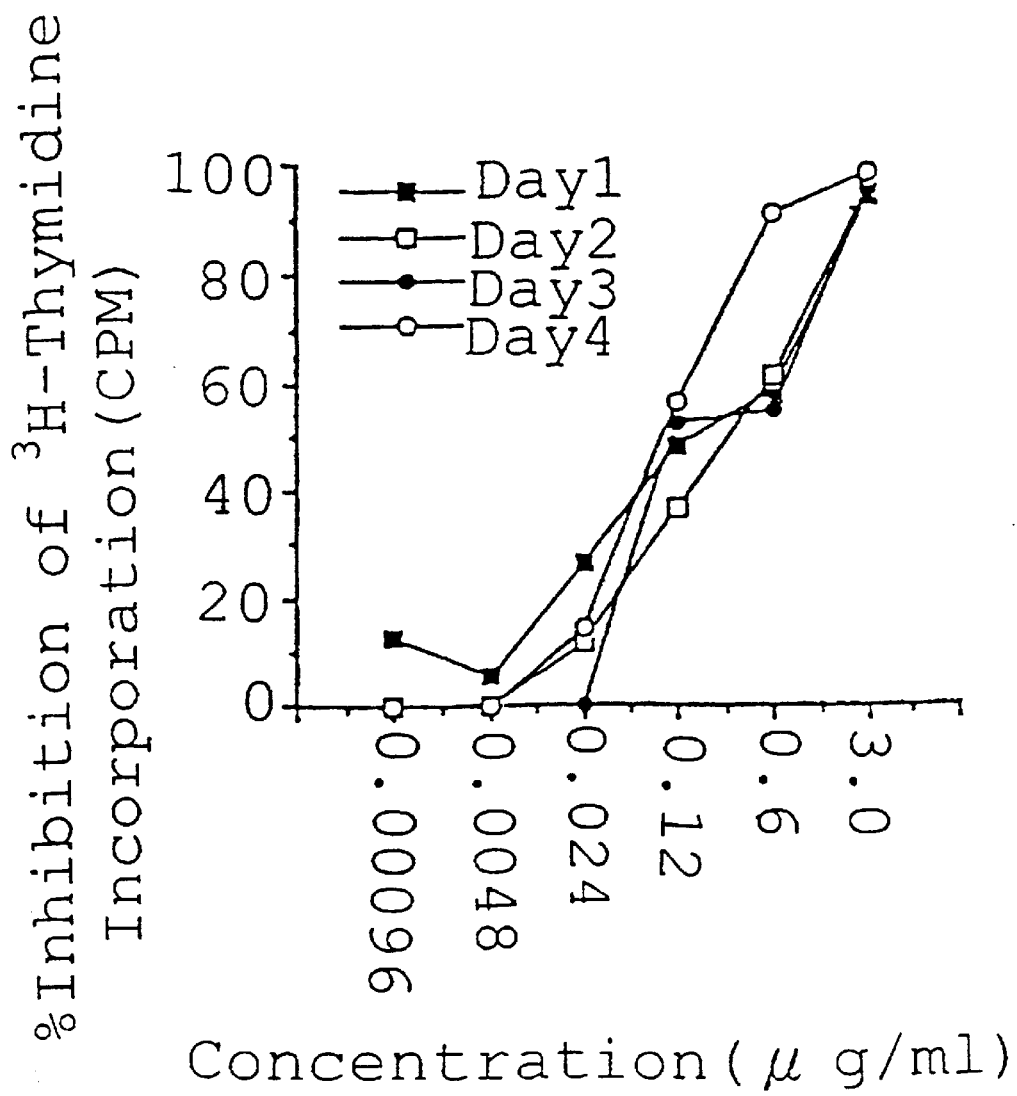
FIG. 6A illustrates the % inhibition of $^3$H-Thymidine incorporation with variation in concentration and time of compound 21 in epidermis carcinoma KB cell.
Figure 6B:
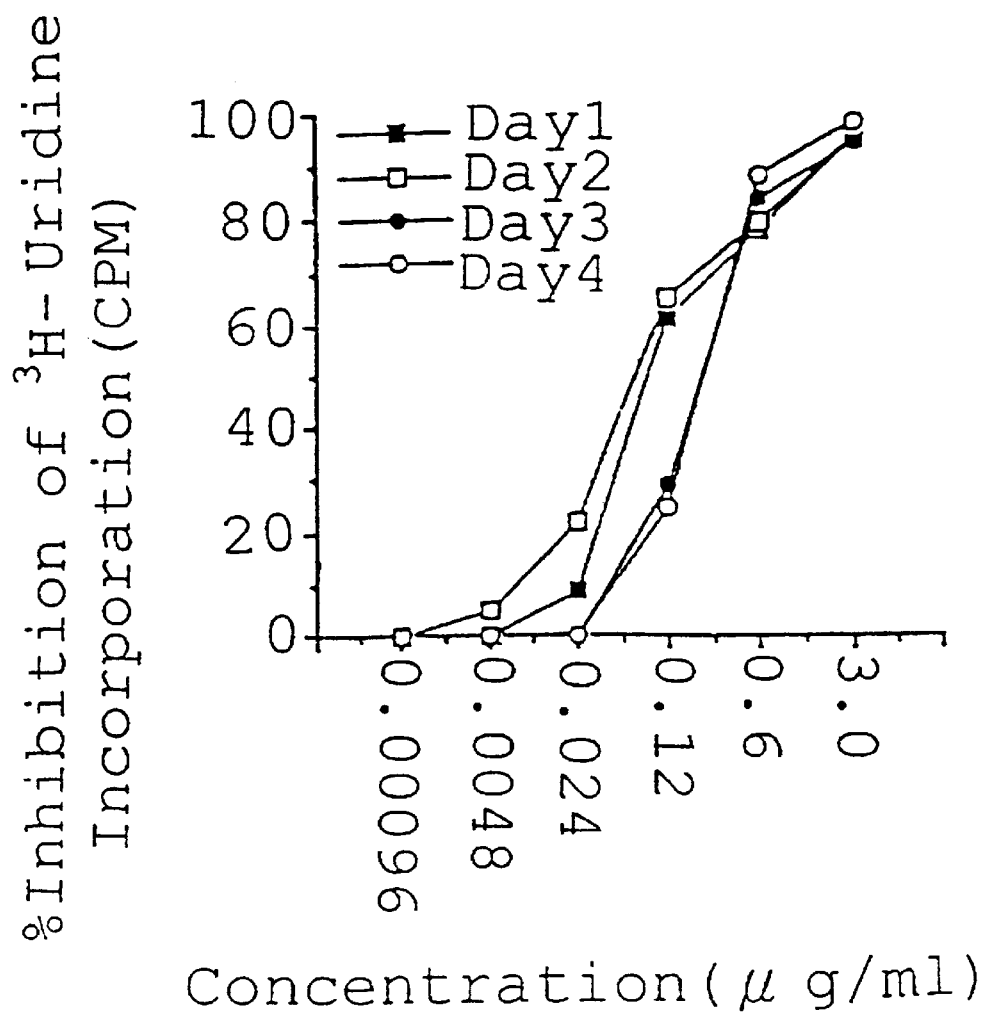
FIG. 6B illustrates the % inhibition of $^3$H-Uridine incorporation with variation in concentration and time of compound 21 in epidermis carcinoma KB cell.
Figure 6C:
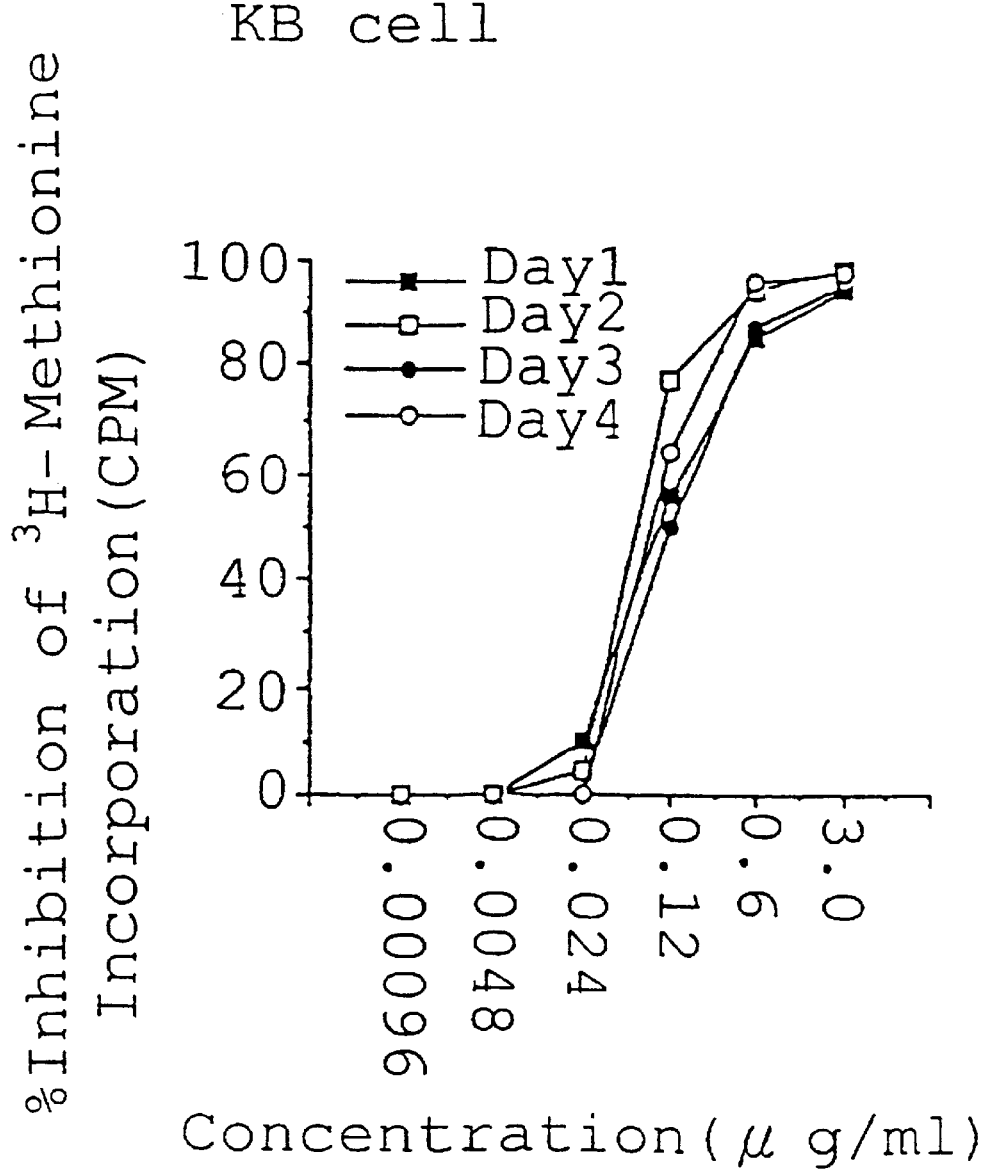
FIG. 6C illustrates the % inhibition of $^3$H-Methionine incorporation with variation in concentration and time of compound 21 in epidermis carcinoma KB cell.

These figures indicate the time-dependent effects of compounds 16, 17 and 21 on DNA, RNA and protein synthesis in the human PLC/PRF/5 cells and show that effects are significant at low concentration but the effects in KB cells are not apparent. The figures show that the inhibition of macromolecular biosynthesis is correlated with the concentration and the period of drug treatment in PLC/PRF/5 cells but the inhibition of macromolecular biosynthesis is only correlated with the concentration of drug treatment in KB cells.

These results indicated that compounds 16, 17 and 21 are potent antitumor agents which suppress cellular DNA, RNA and protein synthesis.

Table 3 hereinbelow summarizes the hydrogen-proton site for several of the compounds of the present invention. Specifically it shows the chemical shift (H-NMR (CDCl$_3$)) as shown in Example 9 (C$_{13}$H$_8$O$_4$). As it is known in the H-NMR technology, m=multiplet; d=doublet; t=triplet, and s=singlet.

TABLE 3

| example | H-1 | H-2 | H-3 | H-4 | H-5 | H-6 | H-7 | H-8 | OH (alls) | OMe (alls) |
|---|---|---|---|---|---|---|---|---|---|---|
| 10 | | 6.19 (d) | | 6.36 (d) | 7.81 (m) | | 7.43–7.55 (m) | 8.08 (dd) | 12.79 | |
| 13 | 7.46 (s) | | | 6.92 (s) | 7.31–7.36 (m) | | 7.37–7.57 (m) | 8.13 (dd) | | |
| 15 | 8.09 (d) | 7.02 (d) | | | 7.69–7.74 (m) | 7.57 (m) | 7.34–7.40 (m) | 8.32 (dd) | | 4.02, 4.04 |
| 17 | 8.22 (d) | 6.92 (dd) | | 6.98 (d) | | 7.19 (dd) | 7.25 (dd) | 7.88 (dd) | | 3.90, 4.02 |
| 18 | 8.03 (d) | 6.90 (dd) | | 6.90 (d) | | 7.27 (dd) | 7.22 (dd) | 7.56 (dd) | | |
| 20 | | 6.74 (dd) | 7.50 (t) | 6.95 (dd) | 6.74 (d) | | 6.85 (dd) | 8.16 (d) | | 3.86, 3.97 |
| 21 | | 6.77 (dd) | 7.66 (t) | 7.00 (dd) | 6.86 (d) | | 6.93 (dd) | 8.02 (d) | 12.84 | |
| 23 | 7.66 (d) | | 7.24 (dd) | 7.34 (d) | 6.80 (d) | | 6.90 (dd) | 8.21 (d) | | 3.89 |
| 24 | 7.44 (d) | | 7.24 (dd) | 7.46 (d) | 6.93 (d) | | 6.88 (dd) | 8.01 (d) | | |
| 26 | 8.23 (d) | 6.93 (dd) | | | 6.84 (d) | | 6.93 (dd) | 8.23 (d) | | 3.93 |
| 27 | 7.98 (d) | 6.86 (dd) | | | 6.82 (d) | | 6.86 (dd) | 7.98 (d) | | |
| 2 | 8.04 (d) | 6.91 (dd) | | 6.87 (d) | 7.82 | 7.43 (m) | 7.59 (m) | 8.16 (dd) | | |

What is claimed is:

1. The process of preparing 3,5-di(2,3-epoxypropoxy)-1-hydroxyxanthone which consists of the following steps:
   a) reacting 1,3,5-trimethoxyxanthone with HI in phenol whereby 1,3,5-trihydroxyxanthone is obtained;
   b) reacting said product from step a) with epichlorohydrin in potassium hydroxide and isolating said 3,5-di(2,3-epoxypropoxy)-1-hydroxyxanthone from the reaction mixture.

* * * * *